(12) United States Patent
Machhammer et al.

(10) Patent No.: US 7,109,374 B2
(45) Date of Patent: Sep. 19, 2006

(54) METHOD FOR THE CONTINUOUS EXTRACTION OF (METH)ACRYLIC ACID

(75) Inventors: Otto Machhammer, Mannheim (DE); Christoph Adami, Weinheim (DE); Claus Hechler, Ludwigshafen (DE); Juergen Schroeder, Ludwigshafen (DE); Volker Schliephake, Schifferstadt (DE); Joachim Thiel, Neustadt (DE); Volker Diehl, Ellerstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/473,102

(22) PCT Filed: Mar. 28, 2002

(86) PCT No.: PCT/EP02/03522

§ 371 (c)(1),
(2), (4) Date: Sep. 29, 2003

(87) PCT Pub. No.: WO02/076917

PCT Pub. Date: Oct. 3, 2002

(65) Prior Publication Data

US 2004/0116736 A1    Jun. 17, 2004

(30) Foreign Application Priority Data

Mar. 28, 2001  (DE) ................. 101 15 277

(51) Int. Cl.
    *C07C 51/42* (2006.01)
(52) U.S. Cl. ...................... 562/600; 562/532
(58) Field of Classification Search ............ 562/512, 562/523, 598, 600
    See application file for complete search history.

(56) References Cited

U.S. PATENT DOCUMENTS

| 5,780,679 | A |   | 7/1998  | Egly et al. |
| 5,855,743 | A |   | 1/1999  | Herbst et al. |
| 5,961,790 | A | * | 10/1999 | Herbst et al. ............. 203/59 |
| 2001/0007043 | A1 | * | 7/2001 | Machhammer et al. ..... 562/600 |

FOREIGN PATENT DOCUMENTS

| DE | 21 36 396  | 2/1973 |
| DE | 24 49 780  | 4/1976 |
| DE | 43 08 087  | 9/1994 |
| DE | 44 36 243  | 4/1996 |
| DE | 198 38 817 | 3/2000 |

* cited by examiner

*Primary Examiner*—Johann Richter
*Assistant Examiner*—Karl Puttlitz
(74) *Attorney, Agent, or Firm*—Oblon, Spivak, McClelland, Maier & Neustadt, P.C.

(57) ABSTRACT

A process for the continuous recovery of (meth)acrylic acid from the reaction gas of a catalytic gas-phase oxidation comprising the following process stages is proposed:
  I quenching of the reaction gas by evaporative cooling using a high-boiling solvent,
  II separation of the (meth)acrylic acid from the quenched reaction gas by absorption into the high-boiling solvent,
  III separation of the solvent laden with (meth)acrylic acid by rectification into a first part-stream IIIA), which contains predominantly (meth)acrylic acid, and into a second part-stream IIIB) which contains predominantly the solvent,
  IV recycling of the stream IIIB) to process stage II and
  V distillative production of (meth)acrylic acid from stream IIIA), all liquid residual streams obtained in process stage V being recycled to process stage I.

7 Claims, 2 Drawing Sheets

METHOD FOR THE CONTINUOUS EXTRACTION OF (METH)ACRYLIC ACID

The present invention relates to a process for the continuous production of (meth)acrylic acid by absorption of (meth)acrylic acid from the reaction gases of a catalytic gas-phase oxidation. Below, the term (meth)acrylic acid means the substances acrylic acid and/or methacrylic acid.

(Meth)acrylic acid is prepared predominantly by catalytic gas-phase oxidation of suitable starting materials, in particular of propene and/or acrolein in the case of acrylic acid or of isobutene and/or methacrolein in the case of methacrylic acid.

A number of possibilities are known for isolating the (meth)acrylic acid from the reaction gases of the catalytic gas-phase oxidation, including separation by absorption into a solvent.

DE-B 21 36 396 discloses that acrylic acid can be isolated from the reaction gases obtained in the catalytic oxidation of propene or acrolein by countercurrent absorption using a mixture of 75% by weight of diphenyl ether and 25% by weight of biphenyl. Furthermore, DE-A 24 49 780 discloses the cooling of the hot reaction gas by partial evaporation of the solvent in a direct condenser (quench apparatus) before the countercurrent absorption. The problem here and in further process steps, in particular in the distillative purification of the (meth)acrylic acid, is the production of solids in the apparatuses, which reduces the availability of the plant. According to DE-A 43 08 087, this solids fraction can be reduced in the case of acrylic acid by adding a polar solvent, such as dimethyl phthalate, in an amount of from 0.1 to 25% by weight to the relatively nonpolar solvent mixture comprising diphenyl ether and biphenyl; this increases the absorptivity of the solvent mixture for the dirt-forming substances. With increasing polarity, however, the solvent takes up increasing amounts of water; in addition, this leads to greater solvent losses via the dilute acid solution.

In the presence of solvents, the polyacrylic acid forms, in regions of higher temperatures as occur in the production of (meth)acrylic acid by the process of the generic type, in particular on the lowermost collecting tray of the absorption column, in the stripping section and bottom of the distillation column and in the heat exchangers, dirt which adheres firmly to the surface of the apparatuses and can be dissolved only with alkalis. Analyses have shown that the dirt comprises a mixture of about 10 to 50% by weight of poly(meth)acrylic acid with solvent as the remainder.

DE-A 198 38 817 relates to a process for the continuous production of (meth)acrylic acid from the reaction gases of a catalytic gas-phase oxidation, which process substantially avoids the susceptibility to soiling in all apparatuses, in particular the production of only alkali-soluble dirt, and thus improves the availability of the plant and cost-efficiency of the process and comprises the following process steps:

(I) quenching of the reaction gas by evaporative cooling using a high-boiling solvent,
(II) separation of the (meth)acrylic acid from the quenched reaction gas by absorption in the high-boiling solvent,
(III) separation of the solvent laden with (meth)acrylic acid into a first part-stream (IIIA), which contains predominantly (meth)acrylic acid, and into a second part-stream (IIIB) which contains predominantly the solvent,
(IV) stripping the part-stream (IIIB) (meth)acrylic acid-free with inert gas,
(V) recycling the purified solvent from part-stream (IIIB) into the absorption stage (II) and
(VI) distillative production of (meth)acrylic acid from part-stream (IIIA), all liquid residual streams obtained in stage (VI) being recycled to the quench stage (I).

Preferably, the temperature in each process stage does not exceed 155° C., preferably 140° C., particularly preferably 120° C.

The term liquid residual streams refers to all liquid streams obtained in the process, except the main product stream.

It has been found that the distillative production of (meth)acrylic acid (stage VI) gives rise to oligomers which to date have been entrained by the liquid residual streams into upstream apparatuses. By avoiding the recycling of the liquid residual streams from the distillative production (stage VI) into the liquid solvent circulation, the soiling of the upstream apparatuses can be substantially prevented. The production of oligomers and hence the production of solids in the apparatuses upstream of process stage (VI) are lower in the process of DE-A 198 38 817; it has therefore been possible for dual-flow or valve trays necessary to date in process stages (II) and (IV) to be replaced by internals having a higher hydrodynamic load capacity, for example dumped packings or stacked packings.

In the apparatuses upstream of the distillation (stage VI of the process of DE-A 198 38 817), the (meth)acrylic acid forms di(meth)acrylic acid in the solvent stream. Owing to the low temperature level in all apparatuses upstream of the distillation, the di(meth)acrylic acid formed in the solvent stream cannot be cleaved back to (meth)acrylic acid, resulting in product losses.

In the process disclosed in DE-A 198 38 817, the (meth)acrylic acid is stripped from the solvent in the stripper, but not the di(meth)acrylic acid. A part of the solvent mixture recycled in process stage (V) and containing di(meth)acrylic acid is used in the known process for recovering the (meth)acrylic acid by extraction from the dilute acid solution obtained in process stage (II). In a direction opposite to the extraction of the (meth)acrylic acid from the dilute acid solution into the solvent, the di(meth)acrylic acid is extracted from the solvent into the dilute acid solution. The dilute acid solution thus contains extracted di(meth)acrylic acid, which is incinerated together with the dilute acid solution, corresponding to a loss of desired product of the order of magnitude of about 1% by weight, based on the total amount of (meth)acrylic acid prepared.

These losses can be prevented or reduced if, according to the invention, di(meth)acrylic acid-containing gas mixtures are heated to elevated temperatures, in particular above 160° C., cleavage to (meth)acrylic acid taking place.

It is an object of the present invention to provide an improved process for the production of (meth)acrylic acid from the reaction gases of a catalytic gas-phase oxidation, which process not only reduces the susceptibility of all apparatuses in the plant to soiling but also substantially avoids product losses due to diacrylic acid formation and further improves the cost-efficiency of the process.

We have found that this process is achieved by a process for the continuous production of (meth)acrylic acid from the reaction gas of a catalytic gas-phase oxidation, comprising the following process stages:

I quenching of the reaction gas by evaporative cooling using a high-boiling solvent,
II separation of the (meth)acrylic acid from the quenched reaction gas by absorption into the high-boiling solvent, III separation of the solvent laden with (meth)acrylic acid into a first part-stream IIIA), which contains predominantly (meth)acrylic acid, and into a second part-stream IIIB) which contains predominantly the solvent, IV recycling of the stream IIIB) to process stage II and V distillative production of (meth)acrylic acid from stream IIIA), all liquid residual streams obtained in process stage V being recycled to process stage I, wherein the separation of the (meth)acrylic acid in process stage III is carried out by rectification.

We have found that separation of the high-boiling solvent laden with (meth)acrylic acid by rectification at temperatures which exceed the maximum temperature of 155° C. defined in the process of DE-A 198 38 817 is entirely possible without the problem of soiling of the plant occurring if the condition that all liquid residual streams obtained in the distillative production (process stage V in the process of the present invention) are recycled to the quench stage I is complied with.

In addition, in contrast to the process disclosed in DE-A 198 38 817, the compressor for the recycle gas, which is used there as stripping gas for stripping (meth)acrylic acid from the solvent stream (process stage IV there), is relieved to an extent of about 30% since stripping is dispensed with in the present process.

Here, solvents are defined as being high-boiling if their boiling point is higher than the boiling point of the main product desired in each case (about 141° C. for acrylic acid and about 161° C. for methacrylic acid, in each case at atmospheric pressure).

Starting mixtures for the present process are the reaction gases from the catalytic gas-phase oxidation of $C_3$-alkanes, $C_3$-alkenes, $C_3$-alkanols and/or $C_3$-alkanals or precursors thereof to (meth)acrylic acid. The process is described below for acrylic acid but is applicable in an analogous manner also to methacrylic acid.

The catalytic gas-phase reaction of propene and/or acrolein to acrylic acid in air or molecular oxygen by known processes, in particular as described in the abovementioned publications, is particularly advantageous. Here, temperatures of from 200 to 450° C. and, if required, superatmospheric pressure are preferably employed. Preferably used heterogeneous catalysts are oxidic multicomponent catalysts based on the oxides of molybdenum, bismuth and iron in the 1st stage (oxidation of propene to acrolein) and on the oxides of molybdenum and vanadium in the 2nd stage (oxidation of acrolein to acrylic acid).

If propane is used as a starting material, it can be converted into a propene/propane mixture by: catalytic oxydehydrogenation as described, for example, in Catalysis Today 24 (1995), 307–313 or U.S. Pat. No. 5,510,558; homogeneous oxydehydrogenation as described, for example, in EP-A-0 253 409, EP-A-0 293 224, DE-A-195 08 558 or EP-A-0 117 146. When a propene/propane mixture is used, propane acts as a diluent gas. Suitable propene/propane mixtures include refinery propene (70% of propene and 30% of propane) of cracker propene (95% of propene and 5% of propane) or propene from a conventional propane dehydrogenation (99.5% of propene and 0.5% of propane). In principle, propene/propane mixtures can be oxidized with mixtures of oxygen and nitrogen of any composition to give acrolein and acrylic acid, as well as propene from an upstream propane dehydrogenation without prior propane/propene separation (20% of propene and 80% of propane).

The conversion of propene into acrylic acid is highly exothermic. The reaction gas, which advantageously contains an inert diluent, for example recycle gas (see below), atmospheric nitrogen, one or more saturated $C_1$–to $C_6$-hydrocarbons, in particular methane and/or propane, and/or steam in addition to the starting materials and products, can therefore take up only a small part of the heat of reaction. Although the type of reactors used is not subject to any restriction per se, tube-bundle heat exchangers which are cooled by means of a salt bath and are filled with the oxidation catalyst are generally used since in this type of heat exchangers the heat liberated in the reaction can be very readily removed by convection and radiation to the cooled tube walls.

The catalytic gas-phase oxidation gives not pure acrylic acid but a gaseous mixture which may contain substantially unconverted acrolein and/or propene, steam, carbon monoxide, carbon dioxide, nitrogen, propane, oxygen, acetic acid, propionic acid, formaldehyde, further acids and aldehydes, maleic acid and maleic anhydride as secondary components in addition to the acrylic acid. Usually, the reaction product mixture contains, based in each case on the total reaction mixture, from 1 to 30% by weight of acrylic acid, from 0.05 to 1% by weight of propene and from 0.01 to 1% by weight of acrolein, from 0.05 to 10% by weight of oxygen, from 0.05 to 2% by weight of acetic acid, from 0.01 to 2% by weight of propionic acid, from 0.05 to 1% by weight of formaldehyde, from 0.05 to 2% by weight of aldehydes, from 0.01 to 0.5% by weight of maleic acid and maleic anhydride together and from 20 to 98, preferably from 50 to 98, % by weight of inert diluent gas. In particular, saturated $C_1$–$C_6$-hydrocarbons, such as from 0 to 95% by weight of methane and/or propane, as well as from 1 to 30% by weight of steam, from 0.05 to 15% by weight of oxides of carbon and from 0 to 95% by weight of nitrogen, based in each case on 100% by weight of the reaction gas, are contained as inert diluent gases.

The process stages for separating the acrylic acid from the reaction mixture are described below:

Process Stage I

The hot reaction gas is cooled by partial evaporation of the solvent in a direct condenser or quench apparatus, prior to the absorption. Venturi scrubbers, bubble columns or spray condensers are particularly suitable for this purpose. The high-boiling secondary components of the reaction gas condense into the unevaporated solvent. In addition, the partial evaporation of the solvent is a purification step for the solvent. In a preferred embodiment of the invention, a part-stream of the unevaporated solvent, preferably from 1 to 10% of the mass flow fed to the absorption column, is taken off and is subjected to a solvent purification. Here, the solvent is distilled over and the high-boiling secondary components remain behind and, after further thickening if necessary, can be disposed of, for example incinerated. This solvent distillation serves for avoiding too high a concentration of high boilers in the solvent stream. The solvent which has distilled over is preferably fed to the laden solvent stream from the absorption column.

Process Stage II

In process stage II, the acrylic acid and a part of the secondary components are separated from the reaction gas by absorption in a high-boiling solvent. The boiling point of the high-boiling solvent is preferably at least 20° C., in particular 50° C., more preferably 70° C., above the boiling point of acrylic acid or methacrylic acid. Preferred solvents, where in the present invention the term solvent also includes solvent mixtures, have boiling points (at atmospheric pressure) of from 180 to 400° C., in particular from 220 to 360° C. Suitable solvents are high-boiling, extremely hydrophobic solvents which contain no polar groups acting externally, for example aliphatic or aromatic hydrocarbons, e.g. middle oil fractions from paraffin distillation, or ethers having bulky groups on the oxygen atom, or mixtures thereof, a polar solvent, such as the 1,2-dimethyl phthalate disclosed in DE-A-43 08 087, advantageously being added to said solvents. Esters of benzoic acid and phthalic acid with straight-chain alkanols of 1 to 8 carbon atoms, such as n-butyl benzoate, methyl benzoate, ethyl benzoate, dimethyl phthalate and diethyl phthalate, heat transfer oils, such as biphenyl, diphenyl ether and mixtures of biphenyl and diphenyl ether or their chlorine derivatives and triarylalkanes, e.g. 4-methyl-4'-benzyldiphenylmethane and its isomers 2-methyl-2'-benzyldiphenyl-methane, 2-methyl-4'-benzyldiphenylmethane and 4-methyl-2'-benzyldiphenyl-methane and mixtures of such isomers are also suitable.

A particularly preferred solvent is a solvent mixture comprising biphenyl and diphenyl ether, preferably in the azeotropic composition, in particular comprising about 25% by weight of biphenyl and about 75% by weight of diphenyl ether, based on 100% by weight of biphenyl and diphenyl ether, for example the commercially available Diphyl®. This solvent mixture preferably furthermore contains a polar solvent, such as dimethyl phthalate, in an amount of from 0.1 to 25% by weight, based on the total solvent mixture. This reduces the susceptibility of the plants to soiling.

Here, the terms high boiler, medium boiler and low boiler and corresponding terms used as adjectives refer to compounds which have a boiling point higher than that of acrylic acid (high boiler), those which have a boiling point roughly equal to that of acrylic acid (medium boiler) and those which have a boiling point lower than that of acrylic acid (low boiler), respectively.

The absorption is effected in a countercurrent absorption column which is preferably equipped with dual-flow trays and/or valve trays or with dumped packings or structured packings and which is fed with solvent from above. The gaseous reaction product and any evaporated solvent from the quench apparatus are passed into the column from below and then cooled to absorption temperature. The cooling is advantageously effected by cooling circulations, i.e. heated solvent is taken off from the column, cooled in heat exchangers and recycled to the column at a point above the take-off point. After the absorption, all high boilers, the major part of the acrylic acid and a part of the low boilers are present in the solvent. The remaining, unabsorbed reaction gas is further cooled in order to separate off the condensable part of the low-boiling secondary components, in particular water, formaldehyde and acetic acid, by condensation thereof. This condensate is referred to below as dilute acid solution. The remaining gas stream predominantly comprises nitrogen, oxides of carbon and unconverted starting materials. A part of said gas stream is preferably recycled as diluent gas, referred to below as recycle gas, to the reaction stages. The atmospheric nitrogen and a part of the uncondensed secondary components are removed as waste gas and preferably incinerated.

Process Stage III

In process stage III, the bottom stream from the countercurrent absorption column, which contains from about 10 to 40% by weight of (meth)acrylic acid, all high boilers and a part of the low boilers in addition to the solvent, is added in the upper region of a rectification column and is separated in the rectification column, at a bottom temperature of from 165 to 210° C., preferably from 180 to 200° C., particularly preferably from 190 to 195° C., and corresponding pressures of from 100 to 500, preferably from 180 to 350, particularly preferably from 250 to 290, mbar, into a top stream which predominantly contains (meth)acrylic acid, all low boilers, a part of the high boilers and residues of the solvent, i.e. in an amount of from about 70 to 95% by weight, and a bottom stream which predominantly contains the solvent and small amounts, i.e. from about 0.1 to 1.5% by weight, of (meth) acrylic acid. The top stream IIIA) is fed for the distillative production of (meth)acrylic acid (process stage V) and the bottom stream IIIB) is recycled in process stage IV to absorption stage II, i.e. is added to the upper region of the countercurrent absorption column.

There are in principle no restrictions with regard to the internals having separation efficiency in the rectification column. It is just as possible to use sieve trays, dual-flow trays, valve trays, dumped packings or stacked packings, but dual-flow trays are preferably used.

The distillative production of (meth)acrylic acid from part-stream IIIA is preferably effected in the following process steps:

V-I corresponding to process stage VII-I of FIG. 1, separation of a residual stream (a) which contains the low boilers, a part of the medium boilers and a part of the high boilers in addition to (meth)acrylic acid and a part-stream (b) which is completely or virtually completely free of low boilers, and V-II corresponding to process stage VI-II of FIG. 1, recovery of (meth)acrylic acid from the part-stream (b).

The separation of acrylic acid from stream IIIA (stage V) is effected by distillation, it being possible in principle to use any type of distillation columns. A dividing wall column having two condensers and an evaporator is advantageously used for this purpose. Particularly suitable internals are dual-flow trays. The dual-flow trays ensure the necessary wetting of the column walls with stabilized liquid. This wetting is supported by spray nozzles which wet otherwise dry surfaces (for example the dome at the top of the column) with stabilized liquid.

The part-stream IIIA is condensed and passes downward through the column V-I, corresponding to process stage VI-I of FIG. 1. In the opposite direction, vapor, predominantly acrylic acid vapor, ascends from the bottom upward and strips the low boilers from the liquid so that the liquid stream (b) entering the bottom is virtually free of low boilers. On the other hand, the medium boilers and high boilers predominantly remain in the liquid during the stripping and reduce the tendency of the acrylic acid to polymerize during the stripping process.

After condensation, a stream (a) rich in low boilers is then taken off at the top of the column. However, since this stream still contains acrylic acid, it is advantageously not discarded from distillation stage V but recycled to quench stage I or absorption stage II.

The preferred operating parameters in the stripping column (process stage V-I) are: top pressure<300, in particular<200, particularly preferably<150, mbar, bottom temperature<150° C., in particular<140° C., particularly preferably<130° C., and acrylic acid concentration at the bottom from 5 to 50, particularly preferably from 20 to 35, %by weight.

The recovery of the acrylic acid from part stream b is preferably effected by separating part stream b into a first part-stream which contains crude acrylic acid and may, if required, be further purified and into a part-stream c. Process stage V-I is preferably effected by distillation in a stripping column with ascending product stream.

The stripping column for process stage V-I and the stripping column with ascending product stream for process stage V-II preferably have a common bottom, as shown for the corresponding process stages VI-I and VI-II of FIG. 1. The part-stream b obtained as a result of process stage V-I in the common bottom of stripping column and stripping column with ascending product stream is separated in the stripping column with ascending product stream in process stage V-II. A part-stream c which predominantly contains the solvent and which, if necessary after purification, in particular by evaporation in a quench, is recirculated to the absorption stage is obtained in the bottom of the column. In the column with ascending product stream, the vapor completely or virtually completely free of low boilers ascends, the medium boilers and high boilers being washed out of the vapor by the liquid reflux. At the top of the column, the vapor is condensed, a part is taken off as product at the top and the remainder is liquid reflux. The product is acrylic acid which is substantially free of low boilers, medium boilers and high boilers. This acrylic acid is referred to as crude acrylic acid.

The crude acrylic acid obtained in stage V contains, based in each case on the crude acrylic acid, preferably from 98 to 99.8, in particular from 98.5 to 99.5, % by weight of acrylic acid and from 0.2 to 2, in particular from 0.5 to 1.5, % by weight of impurities, e.g. acetic acid, aldehydes and maleic anhydride. If the requirements with respect to its purity are not very high, this acrylic acid itself may be used for the esterification.

In a preferred embodiment of the invention, the dilute acid solution which may still contain dissolved acrylic acid is treated by extraction with a small part-stream of the virtually acrylic acid-free solvent (from stage IV). Before it is incinerated, the aqueous stream from the dilute acid solution extraction can be evaporated down, which may be required particularly if there are environmental protection regulations.

However, process stage V, i.e. the recovery of acrylic acid by distillation from the top stream from process stage III, is particularly preferably carried out in a divided wall column or in a multishaft column, as described in the non-prior-published German patent application DE-A 100 02 806.

The invention is illustrated below with reference to a drawing and examples.

Specifically,

Figure 1:
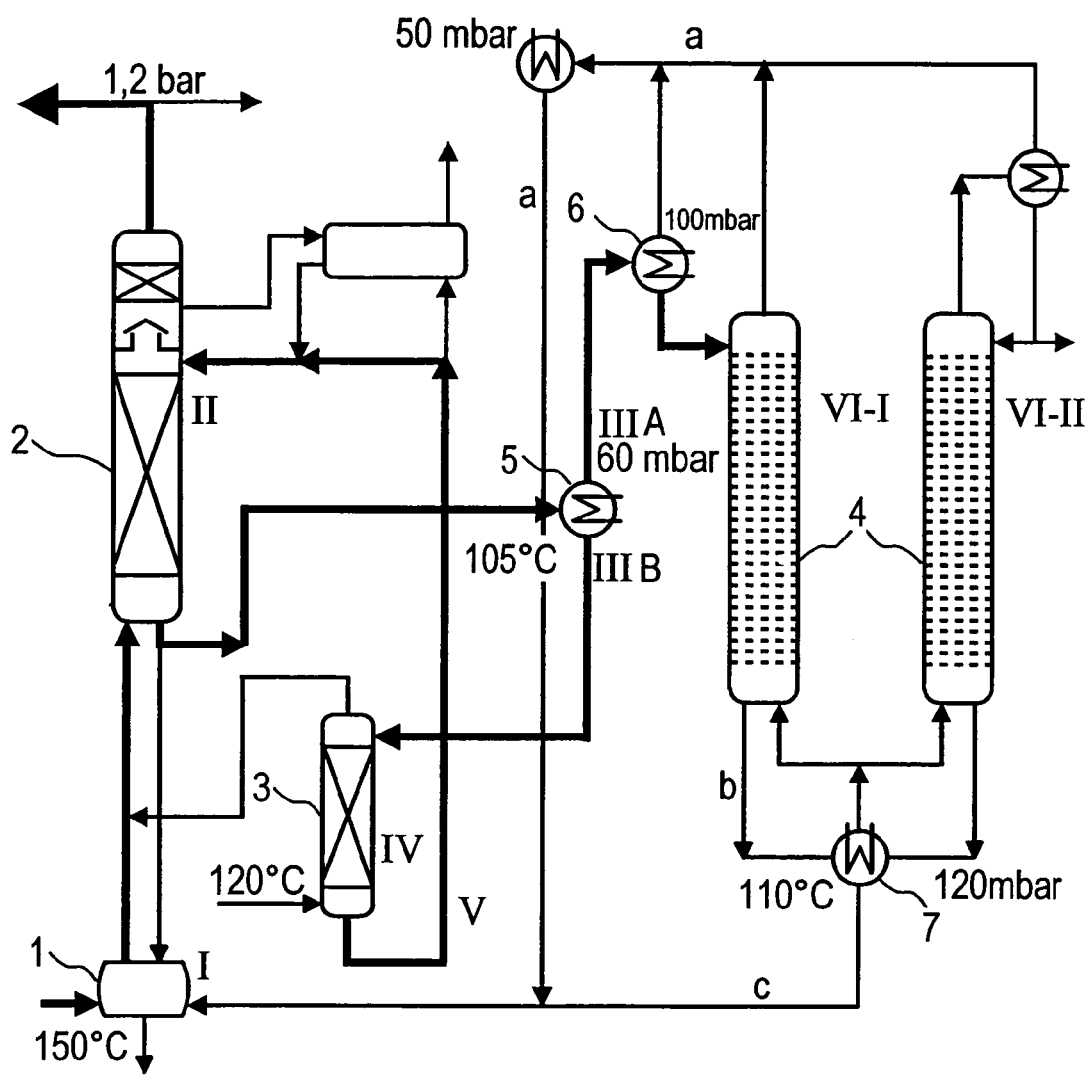
FIG. 1 shows a schematic diagram of a plant according to the prior art.

Below, the recovery of acrylic acid by the conventional process in a plant corresponding to FIG. 1 is first described as a comparative example:

A 2 900 l(S.T.P.)/h gas stream from the gas-phase oxidation to acrylic acid, having a temperature of 270° C. and a pressure of 1.6 bar and comprising the main components (in each case in % by weight)

Nitrogen (75),

Oxygen (3),

Acrylic acid (12),

Water (5),

CO (1), $CO_2$ (3) and the remainder, i.e. further components (1), was cooled to 150° C. in a Venturi quench 1 by direct contact with quench liquid (140–150° C.) which was sprayed in through slits provided in the region of the narrow cross-section of the Venturi tube and which comprised 57.4% by weight of diphenyl ether, 20.7% by weight of biphenyl and 20% by weight of dimethyl o-phthalate, the remainder being other components. That proportion of the quench liquid which remained in the form of liquid drops was then separated, in a downstream drop separator (storage container having a gas pipe leading upward), from the gas phase consisting of reaction gas and evaporated quench liquid and was recycled in a circulation to the Venturi scrubber. A part-steam of the recycled quench liquid was subjected to a solvent distillation, the quench liquid distilling over and high-boiling secondary components remaining behind and being incinerated.

The gas phase at about 150° C. was fed into the lower part of a packed absorption column 2 (3 m high; glass double jacket; internal diameter 50 mm; three packing zones having the lengths (from bottom to top) of 90 cm, 90 cm and 50 cm; the packing zones were thermostated from bottom to top as follows: 90° C., 60° C., 20° C.; the penultimate and the last packing zone were separated by a chimney tray; the packings were stainless steel helices having a helix diameter of 5 mm and a helix length of 5 mm; the absorbent was fed in directly above the middle packing zone) and was exposed to the countercurrent of 2 900 g/h of the absorbent likewise composed of 57.4% by weight of diphenyl ether, 20.7% by weight of biphenyl and 20% by weight of dimethyl o-phthalate and other components as the remainder and added at a temperature of 50° C.

The unabsorbed gas mixture leaving the second packing zone in an upward direction in absorption column 2 was further cooled in the third packing zone in order to separate off the condensable part of the secondary components contained therein, e.g. water and acetic acid, by condensation. This condensate is referred to as dilute acid solution. In order to increase the separation effect, a part of the dilute acid solution was recycled into the absorption column 2 above the third packing zone of absorption column 2 at a temperature of 20° C. The dilute acid solution was removed below the uppermost packing zone, from the chimney tray mounted there. The ratio of recycled to taken-off dilute acid solution was 200 w/w. The dilute acid solution removed also contained 0.8% by weight of acrylic acid in addition to 97.5% by weight of water. This acrylic acid can, if required, be recovered as described in DE-A 196 00 955. 1 600 l(S.T.P.)/h of the gas stream finally leaving absorption column 2 were recycled as recycle gas into the propene oxidation. The remainder was incinerated.

The discharge of absorption column 2 was fed to a forced-circulation flash evaporator 5 which was operated at 60 mbar and 105° C. A 5 230 g/h solvent stream laden with acrylic acid (main components: solvent 61% by weight, acrylic acid 30% by weight, acetic acid 8 118 ppm by weight, maleic anhydride 2 000 ppm by weight) was separated into a first part-stream IIIA of 2 160 g/h, which predominantly contained acrylic acid (main components: solvent 20% by weight, acrylic acid 77% by weight and acetic acid 0.22% by weight) and a second part-stream IIIB of 3 070 g/h, which predominantly contained the solvent (main components: solvent 83% by weight, acrylic acid 5% by weight and acetic acid 636 ppm by weight).

The part-stream IIIB was added at the top of stripping column 3. The stripping gas used was an air stream of 600 l(S.T.P.)/h. The part-stream IIIB from the evaporator was added at the top of stripping column 3; here, stripping column 3 served for removing acrylic acid from the solvent (process stage W). The solvent freed from acrylic acid was taken off from the bottom of the stripping column 3 and recirculated to the top of the absorption column 2. The diacrylic acid content in the solvent was 2.0% by weight.

The part-stream IIIA obtained in the evaporator 5 was condensed in a heat exchanger 6 at 100 mbar, and the condensate was fed to the 28th tray of the rectification column 4 divided into two, i.e. to its stripping section. In the stripping section of the rectification column 4, process stage VI-I took place, i.e. the low boilers were stripped from the part-stream IIIA with acrylic acid vapor by the countercurrent method, whereas the medium boilers and high boilers predominantly remained in the liquid. A stream b virtually free of low boilers (main components: solvent 28% by weight, acrylic acid 71% by weight, acetic acid 721 ppm by weight, maleic anhydride 4 026 ppm by weight) was taken off from the bottom of the stripping section of the rectification column 4. The part-stream b was fed to the common evaporator 7 of the stripping section and of the stripping section with ascending product stream of rectification column 4, and a residual stream c (480 g/h, main components: solvent 87% by weight, acrylic acid 10% by weight, maleic anhydride 7 000 ppm by weight) was taken off from the evaporator 7 and fed to the Venturi quench 1. The vapor stream containing the crude acrylic acid and emerging from the evaporator 7 was fed to the stripping section with ascending product stream of rectification column 4 and was freed from medium boilers and high boilers by the acrylic acid reflux in order to recover the acrylic acid (process stage VI-II). At the top of the stripping section with ascending product stream of rectification column 4, a stream of 420 g/h of the main product acrylic acid was taken off, which main product still contained 1 500 ppm of acetic acid and 50 ppm of maleic anhydride. The vapor from the stripping section of rectification column 4, the apparatus in which process stage VI-I took place, was condensed as residual stream a with 95% by weight of acrylic acid, 0.8% by weight of solvent and 3.6% by weight of acetic acid and was likewise fed to the Venturi quench 1.

After extraction of the dilute acid solution with a part-stream of the solvent stream recirculated in process stage V, the diacrylic acid content of the dilute acid solution fed for incineration was 2.6% by weight.

Figure 2:
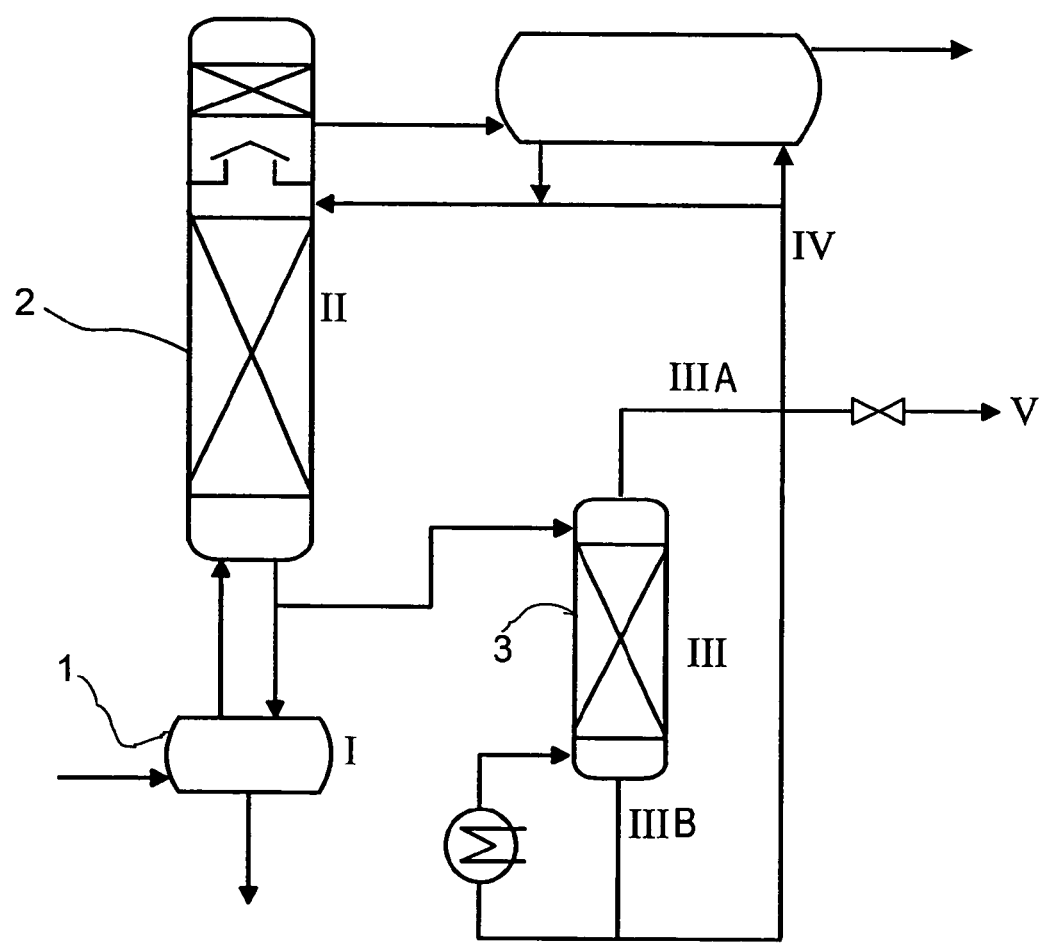
FIG. 2 shows a schematic diagram of a plant according to the invention.

An embodiment of the novel process is described below in conjunction with FIG. 2.

Process stages I and II were unchanged compared with the process from the prior art. In contrast, the bottom liquid from absorption column II was fed to the upper region of a rectification column III, in which the separation of the (meth)acrylic acid-laden solvent into a top stream which contained predominantly, i.e. in an amount of from 70 to 75% by weight, acrylic acid, all low boilers and part of the high boilers and residues of the solvent and a bottom stream which contained the predominant part of the solvent and residual amounts of from about 0.1 to 1.5% by weight of (meth)acrylic acid was carried out in process stage III. The rectification column was equipped with 9 dual-flow trays and was operated at a bottom temperature of 195° C. The liquid bottom stream IIIB) contained 0.8% by weight of diacrylic acid and was recycled to absorption stage II in process step IV. After the extraction of the dilute acid solution with a part-stream of the solvent stream recycled in process stage IV, the diacrylic acid content of the dilute acid solution fed for incineration was 1.0% by weight.

The top stream IIIA) in vapor form was further fed to the distillation (process stage V), which was designed as in the comparative example and operated under the same process conditions and led to a product having the same quality as in the comparative example.

In the novel process, it was thus possible, as a result of the high bottom temperature in process stage III, to more than halve the acrylic acid losses via the dilute acid solution in the form of diacrylic acid. For the process as a whole, this means an increase of 0.5% in the product yield. Since acrylic acid is produced in production plants on a 100 000 metric tons per year scale, the increase of 0.5% in the product yield is a significant economic advantage.

We claim:

1. A process for the continuous production of (meth)acrylic acid from the reaction gas of a catalytic gas-phase oxidation producing (meth)acrylic acid, comprising the following process stages:
   I quenching of the reaction gas by evaporative cooling using a high-boiling solvent,
   II separation of the (meth)acrylic acid from the quenched reaction gas by absorption into the high-boiling solvent to produce a high boiling solvent laden with (meth)acrylic acid, followed by as the next succeeding separation stage,
   III separation of the high boiling solvent laden with (meth)acrylic acid into a first part-stream (IIIA) in vapor form, which contains predominantly (meth)acrylic acid, and into a liquid second part-stream (IIIB) which contains predominantly the high-boiling solvent,
   IV recycling of the stream (IIIB) to process stage II and
   V distillative production of (meth)acrylic acid from stream (IIIA), wherein all liquid residual streams obtained in process stage V are recycled to process stage I,
   wherein process stage III is carried out by rectification.

2. A process as claimed in claim 1, wherein process stage III is carried out in a rectification column at a bottom temperature of from 165 to 210° C.

3. A process as claimed in claim 1, wherein process stage III is carried out in a rectification column at a bottom temperature of from 180 to 200° C.

4. A process as claimed in claim 1, wherein process stage III is carried out in a rectification column at a bottom temperature of from 190 to 195° C.

5. A process as claimed in claim 1, wherein a rectification column having dual-flow trays is used in process stage III.

6. A process as claimed in claim 1, wherein process stage V is carried out in a multishaft column.

7. A process as claimed in claim 1, wherein process stage III is carried out in a rectification column at a bottom temperature sufficiently high to cleave di(meth)acrylic acid to (meth)acrylic acid.

* * * * *